United States Patent [19]

Tsukada et al.

[11] Patent Number: 4,996,050

[45] Date of Patent: Feb. 26, 1991

[54] FIBRINOLYTIC ACTIVITY ENHANCER

[75] Inventors: Minoru Tsukada, Osaka; Kenji Tanaka, Nara; Yoshiro Iga, Osaka, all of Japan

[73] Assignee: Green Cross Corporation, Osaka, Japan

[21] Appl. No.: 252,468

[22] Filed: Oct. 3, 1988

[30] Foreign Application Priority Data

Oct. 1, 1987 [JP] Japan .................................. 62-248937

[51] Int. Cl.$^5$ ............................................ A61K 37/547
[52] U.S. Cl. ................................ 424/94.2; 424/94.63; 424/94.64
[58] Field of Search ............................... 435/212, 215; 424/94.63, 94.64, 101, 942

[56] References Cited

U.S. PATENT DOCUMENTS

Re. 32,271  10/1986  Husain et al. ........................ 435/215

FOREIGN PATENT DOCUMENTS 0139447  9/1984  European Pat. Off. .
0154272  2/1985  European Pat. Off. .
0253241  7/1987  European Pat. Off. .

OTHER PUBLICATIONS

Pannell et al., cited in Biol. Abstracts vol. 83(9), 82602(1987).
Haemostasis 18: Suppl. 1, pp. 127–138 (1988), V. V. Kakkar et al.
Haemostasis 18: Suppl. 1, pp. 139–156 (1988), V. Tilsner et al.
J. Biochem 82, 1495–1498 (1977), T. Morita et al.
J. Biol. Chem., vol. 260, No. 22, pp. 12377–12381, (1985) S. Kasai et al.

Primary Examiner—Jacqueline Stone
Attorney, Agent, or Firm—Sughrue, Mion, Zinn, Macpeak & Seas

[57] ABSTRACT

A fibrinolytic activity enhancer for signal-chain pro-urokinase comprising plasminogen as an active ingredient is disclosed. The fibrinolytic activity enhancer of the present invention enhances the fibrinolytic activity of single-chain pro-urokinase without causing systemic fibrinolysis. Thus, it is highly useful in the treatment of thrombosis and obstructive diseases.

12 Claims, No Drawings

FIBRINOLYTIC ACTIVITY ENHANCER

FIELD OF THE INVENTION

This invention relates to a fibrinolytic activity enhancer for single-chain pro-urokinase which comprises plasminogen as an active ingredient.

BACKGROUND OF THE INVENTION

Streptokinase and urokinase have been widely applied to the treatment of thrombosis and obstructive diseases including cerebral thrombosis, peripheral arterial obstruction, peripheral venous obstruction and acute myocardial infarction.

However, it has been pointed out that the application of these drugs would be accompanied by some side effects such as a decrease in circulating fibrinogen or hemorrhage. Therefore, there have been attempts to develop a thrombolytic drug which is more safe and more effective than conventional ones and yet exerts a specific effect on fibrin.

The signle-chain structure of single-chain prourokinase, which is one of the thrombolytic drugs having specific attraction to fibrin, can be incised by treating the same with plasmin. Thus, urokinase of double-chain type, which is the conventionally known urokinase (hereinafter referred to as double-chain urokinase) is obtained.

A plasminogen activator (PA) such as urokinase activates plasminogen circulating in blood to convert it to plasmin which in turn can dissolve thrombi. It is the thrombolytic effect caused by the activation of plasminogen that plays an important role in thrombolysis.

Since double-chain urokinase is an activating type, it mainly activates plasminogen in blood and thereby causes lysis of thrombi. Accordingly, double chain urokinase can cause systemic fibrinolysis, for example, by the decomposition of fibrinogen by the produced, circulating plasmin. In contrast thereto, the plasminogen-activating effect of single-chain prourokinase is significantly lower than that of double-chain urokinase. Even if single-chain pro-urokinase should activate circulating plasminogen to form a trace amount of plasmin, the activity of the plasmin is inhibited by $\alpha 2$-PI which is a plasmin inhibitor exerting an immediate-type, intense antiplasmin activity. Thus, single-chain prourokinase hardly activates plasminogen. In addition, since single-chain pro-urokinase has a high affinity for fibrin, its thrombolytic effect is mainly caused by the activation of plasminogen in thrombi and systemic fibrinolysis is rarely induced.

On the other hand, it is possible to enhance the fibrinolytic activity of urokinase by increasing the amount of available plasminogen, which is the substrate of the plasminogen activator, i.e., urokinase, to thereby promote the formation of plasmin. It is well known that the combined use of double-chain urokinase and plasminogen would enhance the former's fibrinolytic activity (cf. V.V. Kakkar, M. F. Scully, Haemostasis, 18, suppl. 1, 127 (1988); and V. Tilsner, G. Witte, ibid., 139 (1988)).

SUMMARY OF THE INVENTION

An object of the present invention is to provide a fibrinolytic activity enhancer for single-chain pro-urokinase comprising plasminogen as an active ingredient.

The present inventors have conducted extended studies and consequently found that the combined use of sigle-chain pro-urokinase and plasminogen enhances the fibrinolytic activity of the single-chain pro-urokinase without causing any systemic fibrinolysis.

DETAILED DESCRIPTION OF THE INVENTION (i) Single-chain pro-urokinase

The single-chain pro-urokinase to be used in the present invention exerts little fibrinolytic activity as such. However, it is converted into double-chain urokinase by treatment with an enzyme such as plasmin and it then exerts a fibrinolytic activity. Further, it per se exerts only a little fibrinolytic activity in the presence of fibrin.

Typical examples of the single-chain pro-urokinase to be used in the present invention are those of a molecular weight of 50,000 to 55,000 having a single-chain peptide bond structure.

Examples of such single-chain pro-urokinase as described above include the one comprising 411 constituting amino acids whose amino acid sequence will be illustrated in Table 4 below (cf. EP-A-139447).

The above single-chain pro-urokinase may originate from any source, without limitation. For example, it may be obtained by a cell culture method or a genetic engineering technique, disclosed in EP-A-139447 and EP-A-154272 respectively.

The term "single-chain pro-urokinase" as used herein includes not only the above mentioned on but also its derivatives. Examples of such derivatives include protein molecules wherein the whole or some part of the epidermal growth factor domain of single-chain prourokinase is deleted or substituted with other amino acid residue(s) (cf. EP-A-253241). Therefore, the expression "single-chain pro-urokinase" as used herein means single-chain pro-urokinase per se as well as the derivatives thereof as described above, unless otherwise noted.

Single-chain pro-urokinase derivatives usually have a molecular weight of 40,000 to 50,000 and a single-chain peptide bond structure, similar to the single-chain pro-urokinase per se. Its expression mechanism of the fibrinolytic activity is also the same as that of the single-chain pro-urokinase per se.

These derivatives may be obtained by, for example, genetic engineering techniques.

Regarding the specific activity of the single-chain pro-urokinase, it shows no activity as such in the synthetic substrate method (cf. T. Morita et al., J. Biochem. 82, 1495–1498 (1977), S. Kasai et al., J. Biol. Chem. 260, 12377–12381 (1985)). It shows a specific activity of 100 to 1,000 UK unit/mg in the presence of fibrin and that of 80,000 to 200,000 UK unit/mg after treating with plasmin.

(ii) Plasminogen

The plasminogen to be used in the present invention is not particularly restricted. Examples thereof include those obtained from human or animal serum, plasma, ascites fluid, placenta extract or placenta tissue extract as well as those purified from plasminogen-containing fractions obtained by Cohn's cold alcohol fractionation and those prepared through genetic engineering techniques.

Typical examples of methods for purifying plasminogen include the purification of plasmin-free plasminogen with the use of fixed aprotinin (cf. JP-A-55-153592; the term "JP-A" used herein means an "unexamined published Japanese patent application.") and the purification of plasminogen with the use of lysine/Sepharose (cf. Science, 170, 1095 (1970)).

The specific activity of the plasminogen ranges from 10 to 100 cu (casein unit)/mg.

(iii) Administration and dose

The single-chain pro-urokinase may be administered in such an amount as to give a blood concentration thereof of 0.02 to 2 μg/ml, which corresponds to a dose of approximately 300 to 36,000 UK (in terms of urokinase)/kg body weight in the case of intravenous administration, preferably a blood concentration of 0.1 to 1 μg/ml. The administration may be effected by, for example, intravenous injection, intravenous drip infusion, or intracoronary injection.

The plasminogen may be administered in such an amount as to give a blood concentration thereof of 0.05 to 5.0 cu/ml, which corresponds to a dose of approximately 10 to 100 cu/kg body weight in the case of intravenous administration, preferably a blood concentration of 0.1 to 1 cu/ml. The administration may be effected by, for example, intravenous injection or intracoronary injection.

Single-chain pro-urokinase and plasminogen may be administered separately or simultaneously. Specifically, the administration may be carried out by (1) intravenously or intracoronarily injecting single-chain pro-urokinase 1 minute to 3 hours after intravenously or intracoronarily injecting plasminogen; (2) intravenously or intracoronarily injecting plasminogen 1 minute to 3 hours after intravenously or intracoronarily injecting single-chain pro-urokinase; (3) intravenously or intracoronarily injecting plasminogen followed by intravenous drip infusion of single-chain pro-urokinase; and (4) intravenously or intracoronarily injecting plasminogen several times during intravenous drip infusion of single-chain pro-urokinase.

For example, combinations of 0.02 to 0.2 μg/ml of single-chain pro-urokinase and 0.1 to 2.5 cu/ml of plasminogen, 0.2 to 0.6 μg/ml of the former and 0.1 to 1 cu/ml of the latter and 0.6 to 2 μg/ml of the former and 0.1 to 0.5 cu/ml of the latter are recommended.

The combined use of single-chain pro-urokinase and plasminogen at a specific ratio can enhance the fibrinolytic activity of the single-chain pro-urokinase without causing any abnormal enhancement of the fibrinolytic activity of the single-chain pro-urokinase, i.e., systemic fibrinolysis.

Accordingly, the fibrinolytic activity enhancer of the present invention enables lowering the dose of the single-chain pro-urokinase, which might relieve the side effects of the same including any systemic fibrinolysis.

Thus, it is believed that the fibrinolytic activity enhancer for single-chain pro-urokinase of the present invention is highly useful in the treatment of thrombosis with the use of single-chain pro-urokinase.

To further illustrate the present invention, and not by way of limitation, the following Examples will be given.

EXAMPLE 1

Preparation of single-chain pro-urokinase

Cultured human renal cells were incubated in a serum-free medium containing 0.1% of human plasma albumin for three days. the incubation medium was centrifuged and the supernatant was frozen and preserved. The pooled incubation supernatant was adjusted to pH 5.5 and brought into contact with CM-Sephadex C-50. After washing the column with a 0.16 M phosphate buffer (pH 5.5), the adsorbed single-chain pro-urokinase was eluted with a 0.16 M phosphate buffer (pH 8.5).

Separately, mouse BALB/c spleen cells, which had been preliminarily immunized with single-chain pro-urokinase, were fused with mouse myeloma cells. Among the hybridomas thus obtained, a clone showing a high productivity of an antibody for single-chain pro-urokinase was selected. A monoclonal antibody for single-chain pro-urokinase was recovered from the incubation medium of the above fused cells. This monoclonal antibody was fixed onto BrCN-activated Sepharose 4B (mfd. by Pharmacia).

This monoclonal antibody column was equilibrated with 0.1 M phosphate buffer (pH 7.0) containing 0.4 M of NaCl and the eluate containing the single-chain pro-urokinase precursor was brought into contact therewith. After washing the column with a 0.1 M phosphate buffer (pH 7.0) containing 0.4 M of NaCl, the adsorbed urokinase precursor was eluted with a 0.2 M glycine/HCl aqueous solution (pH 2.5) containing 0.5 M of NaCl. The eluate was filtered under sterile conditions and lyophilized to thereby give highly purified single-chain pro-urokinase having a specific activity of 150,000 (UK unit)/mg in terms of urokinase.

This purified product showed a single bond corresponding to a molecular weight of 54,000 in SDS/polyacrylamide gel electrophoresis. The amino acid sequence thereof is shown in Table 4.

A plasminogen-containing fraction obtained by Cohn's cold ethanol fractionation was suspended in a solution containing 1% (w/v) of sodium chloride and 1% (w/v) of glycine. After slightly stirring, the resulting suspension was centrifuged to thereby separate the supernatant. This supernatant was treated according to a method reported by Deutch D.G. et al. (cf. Science, 170, 1095 (1970)). Namely, the supernatant was poured into a lysine/Sepharose column and thus the plasminogen was adsorbed by the column. Then contaminating proteins were washed away with a physiological saline solution and the adsorbed plasminogen was eluted with a solvent (pH 7.2) containing 0.25 M of lysine and 0.9 % of glycine. The specific activity of the plasminogen thus obtained was 21 cu/mg.

Preparation of human normal plasma

Citrated fresh blood collected from a normal subject was centrifuged at 2,500 rpm for ten minutes and the supernatant was collected.

Formation of artificial thrombus $^{125}$I-labeled human fibrinogen (IRC, 0.1 mCi/ml) in 0.25 M $CaCl_2$/saline was added to 5 ml of normal human blood to thereby form clots.

Dissolution of artificial thrombus

100 μl of single-chain pro-urokinase and 100 μl of plasminogen were added to 2,300 μl of human plasma and the artificial thrombi formed above were introduced thereto. After 0, 1, 2, 3 and 4 hours, the resulting solution was collected and the radioactivity of a representative portion thereof was determined (Table 1-after 4 hours). The residual supernatant was subjected to the determinations of the plasmin and urokinase activities (data of Examples 2 and 3). The thrombolytic ratio was calculated by substracting the radioactivity leaking into the plasma from the initial radioactivity of the artificial thrombi.

Determination of urokinase activity

It was determined by the synthetic substrate method with the use of Glt-Gly-Arg-MCA (p-methylcumarylamide).

Determination of plasmin activity

It was determined by the synthetic substrate method with the use of Boc-Val-Leu-Lys-MCA (see above).

Test method

100 μl portions of single-chain pro-urokinase and plasminogen were added to 2,300 μl of plasma. Then, artificial thrombi, which had been preliminarily formed from blood, were introduced therein and heated to 37° C. for four hours.

The pharmacological effect (fibrinolytic activity) of the combined use of the urokinase precursor and plasminogen in the presence of thrombi was examined in vitro. Table 1 shows the results.

TABLE 1

| Thrombolytic ratio (%) | Plasminogen (cu/ml) | |
|---|---|---|
| | 0 | 0.75 |
| Single-chain | 0 | | |
| pro-urokinase | 0.027 | <1 | <1 |
| (μg/ml) | 0.09 | 8 | 17 |
| | 0.27 | 23 | 35 |

As is apparent from the results shown in Table 1, it was found that the thrombolytic effect was enhanced when single-chain pro-urokinase was administered in a concentration not less than 0.09 μg/ml in combination with plasminogen.

EXAMPLE 2

A side effect (blood urokinase activity) of the combined use of single-chain pro-urokinase and plasminogen both prepared in Example 1 in the presence of thrombi was examined in vitro. The administration concentrations were the same as those shown in Example 1. Table 2 shows the results.

TABLE 2

| Blood urokinase activity (UK unit/ml) | Plasminogen (cu/ml) | |
|---|---|---|
| | 0 | 0.75 |
| Single-chain | 0 | 0 | 0 |
| pro-urokinase | 0.06 | 0 | 0 |
| (μg/ml) | 0.2 | 0 | 0 |
| | 0.6 | 0.02 | 0.02 |

From the results shown in Table 2, it was found that no increase of blood urokinase activity due to doulbe-chain urokinase was observed even when single-chain pro-urokinase and plasminogen were used in such concentrations as to enhance the thrombolytic effect. Therefore, it is supposed that single-chain pro-urokinase is scarcely converted to double-chain urokinase in blood.

EXAMPLE 3

A side effect (blood plasmin activity) of the combined use of single-chain pro-urokinase and plasminogen both prepared in Example 1 in presence of thrombi was examined in vitro. The administration concentrations were the same as those as shown in Example 1. Table 3 shows the results.

TABLE 3

| Blood plasmin activity (%) (cu/ml) | Plasminogen (cu/ml) | |
|---|---|---|
| | 0 | 0.75 |
| Single-chain | 0 | 0 | 0 |
| pro-urokinase | 0.06 | 0 | 0 |
| (μg/ml) | 0.2 | 0 | 0 |
| | 0.6 | 0.1 | 0.1 |

It can be seen from the results shown in Table 3 that no increase of blood plasmin activity was observed even when single-chain pro-urokinase and plasminogen were used in such concentrations as to enhance the thrombolytic effect. Therefore, it is presumed that the exceeding decomposition of fibrin in plasma by circulating plasmin is prevented and the combined use of single-chain pro-urokinase and plasminogen enhances the fibrinolytic activity of the single-chain pro-urokinase without causing any systemic fibrinolysis.

TABLE 4

```
1                                           11
Ser—Asn—Glu—Leu—His—Gln—Val—Pro—Ser—Asn—Cys—Asp—Cys—Leu—Asn—Gly—Gly—Thr—Cys—Val—
21                                          31
Ser—Asn—Lys—Tyr—Phe—Ser—Asn—Ile—His—Trp—Cys—Asn—Cys—Pro—Lys—Lys—Phe—Gly—Gly—Gln—
41                                          51
His—Cys—Glu—Ile—Asp—Lys—Ser—Lys—Thr—Cys—Tyr—Glu—Gly—Asn—Gly—His—Phe—Tyr—Arg—Gly—
61                                          71
Lys—Ala—Ser—Thr—Asp—Thr—Met—Gly—Arg—Pro—Cys—Leu—Pro—Trp—Asn—Ser—Ala—Thr—Val—Leu—
81                                          91
Gln—Gln—Thr—Tyr—His—Ala—His—Arg—Ser—Asp—Ala—Leu—Gln—Leu—Gly—Leu—Gly—Lys—His—Asn—
101                                         111
Tyr—Cys—Arg—Asn—Pro—Asp—Asn—Arg—Arg—Pro—Trp—Cys—Tyr—Val—Gln—Val—Gly—Leu—Lys—
121                                         131
Pro—Leu—Val—Gln—Glu—Cys—Met—Val—His—Asp—Cys—Ala—Asp—Gly—Lys—Lys—Pro—Ser—Ser—Pro—
141                                         151
Pro—Glu—Glu—Leu—Lys—Phe—Gln—Cys—Gly—Gln—Lys—Thr—Leu—Arg—Pro—Arg—Phe—Lys—Ile—Ile—
161                                         171
Gly—Gly—Glu—Phe—Thr—Thr—Ile—Glu—Asn—Gln—Pro—Trp—Phe—Ala—Ala—Ile—Tyr—Arg—Arg—His—
181                                         191
Arg—Gly—Gly—Ser—Val—Thr—Tyr—Val—Cys—Gly—Gly—Ser—Leu—Ile—Ser—Pro—Cys—Trp—Val—Ile—
201                                         211
Ser—Ala—Thr—His—Cys—Phe—Ile—Asp—Tyr—Pro—Lys—Lys—Glu—Asp—Tyr—Ile—Val—Tyr—Leu—Gly—
221                                         231
Arg—Ser—Arg—Leu—Asn—Ser—Asn—Thr—Gln—Gly—Glu—Met—Lys—Phe—Glu—Val—Glu—Asn—Leu—Ile—
241                                         251
Leu—His—Lys—Asp—Tyr—Ser—Ala—Asp—Thr—Leu—Ala—His—His—Asn—Asp—Ile—Ala—Leu—Leu—Lys—
261                                         271
Ile—Arg—Ser—Lys—Glu—Gly—Arg—Cys—Ala—Gln—Pro—Ser—Arg—Thr—Ile—Gln—Thr—Ile—Cys—Leu—
281                                         291
Pro—Ser—Met—Tyr—Asn—Asp—Pro—Gln—Phe—Gly—Thr—Ser—Cys—Glu—Ile—Thr—Gly—Phe—Gly—Lys—
```

TABLE 4-continued

```
301                                           311
Glu—Asn—Ser—Thr—Asp—Tyr—Leu—Tyr—Pro—Glu—Gln—Leu—Lys—Met—Thr—Val—Val—Lys—Leu—Ile—
321                                           331
Ser—His—Arg—Glu—Cys—Gln—Gln—Pro—His—Tyr—Tyr—Gly—Ser—Glu—Val—Thr—Thr—Lys—Met—Leu—
341                                           351
Cys—Ala—Ala—Asp—Pro—Gln—Trp—Lys—Thr—Asp—Ser—Cys—Gln—Gly—Asp—Ser—Gly—Gly—Pro—Leu—
361                                           371
Val—Cys—Ser—Leu—Gln—Gly—Arg—Met—Thr—Leu—Thr—Gly—Ile—Val—Ser—Trp—Gly—Arg—Gly—Cys—
381                                           391
Ala—Leu—Lys—Asp—Lys—Pro—Gly—Val—Tyr—Thr—Arg—Val—Ser—His—Phe—Leu—Pro—Trp—Ile—Arg—
401                                           411
Ser—His—Thr—Lys—Glu—Glu—Asn—Gly—Leu—Ala—Leu
```

While the invention has been described in detail and with reference to specific embodiments thereof, it will be apparent to one skilled in the art that various changes and modifications can be made therein without departing from the spirit and scope thereof.

What is claimed is:

1. A fibrinolytic activity enhancer for single-chain pro-urokinase which comprises single-chain pro-urokinase in an amount to provide a dose of approximately 300 to 36,000 UK/kg of body weight (in terms of urokinase) and plasminogen as an active ingredient in an amount effective to enhance the fibrinolytic activity of single-chain pro-urokinase without causing systemic fibrinolysis, and a pharmaceutically acceptable carrier.

2. A process for enhancing the fibrinolytic activity of single-chain pro-urokinase which comprises administering to a patient single-chain pro-urokinase in a dose of approximately 300 to 36,000 UK/kg of body weight (in terms of urokinase) and an amount of plasminogen effective to enhance the fibrinolytic activity of the single-chain pro-urokinase.

3. A process for enhancing the fibrinolytic activity of single-chain pro-urokinase administered in a dose of approximately 300 to 36,000 UK/kg of body weight (in terms of urokinase) which comprises administering to a patient an amount of plasminogen effective to enhance the fibrinolytic activity of the single-chain pro-urokinase.

4. The process of claim 2 wherein the specific activity of the single-chain pro-urokinase is of 80,000 to 200,000 UK units/mg after treatment with plasmin.

5. The process of claim 3 wherein the specific activity of the single-chain pro-urokinase is of 80,000 to 200,000 UK units/mg after treatment with plasmin.

6. The process of claim 2 wherein the specific activity of the plasminogen is from 10 to 100 cu/mg.

7. The process of claim 3 wherein the specific activity of the plasminogen is from 10 to 100 cu/mg.

8. The process of claim 2 wherein the plasminogen is administered in a dose of approximately 10 to 100 cu/kg of body weight.

9. The process of claim 3 wherein the plasminogen is administered in a dose of approximately 10 to 100 cu/kg of body weight.

10. The process of claim 2 wherein the single-chain pro-urokinase has an activity of 80,000 to 200,000 UK units/mg (in terms of urokinase) and the plasminogen has an activity of approximately 10 to 100 cu/mg, with the single-chain pro-urokinase being administered to give a blood concentration of 0.02 to 0.2 µg/ml and the plasminogen being administered to give a blood concentration of 0.1 to 2.5 cu/ml, or the single-chain pro-urokinase being administered to give a blood concentration of 0.2 to 0.6 µg/ml with the plasminogen being administered to give a blood concentration of 0.1 to 1 cu/ml, or the single-chain pro-urokinase being administered to give a blood concentration of 0.6 to 2 µg/ml with plasminogen being administered to give a blood concentration of 0.1 to 0.5 cu/ml.

11. The process of claim 3 wherein the single-chain pro-urokinase has an activity of 80,000 to 200,000 UK units/mg (in terms of urokinase) and the plasminogen has an activity of approximately 10 to 100 cu/mg, with the single-chain pro-urokinase being administered to give a blood concentration of 0.02 to 0.2 µg/ml and the plasminogen being administered to give a blood concentration of 0.1 to 2.5 cu/ml, or the single-chain pro-urokinase being administered to give a blood concentration of 0.2 to 0.6 µg/ml with the plasminogen being administered to give a blood concentration of 0.1 to 1 cu/ml, or the single-chain pro-urokinase being administered to give a blood concentration of 0.1 to 1 cu/ml, or the single-chain pro-urokinase being administered to give a blood concentration of 0.6 to 2 µg/ml with plasminogen being administered to give a blood concentration of 0.1 to 0.5 cu/ml.

12. A process for treating thrombosis which thrombosis which comprises administering to a patient single-chain pro-urokinase in a dose of 300 to 36,000 UK units/kg of body weight (in terms of urokinase) together with plasminogen in an amount effective to enhance the fibrinolytic activity of the single-chain prourokinase without causing systemic fibrinolysis.

* * * * *